United States Patent
Bar et al.

(10) Patent No.: US 9,527,234 B2
(45) Date of Patent: Dec. 27, 2016

(54) STENT THERMOFORMING APPARATUS AND METHODS

(71) Applicant: INSPIREMD, LTD, Tel Aviv (IL)

(72) Inventors: Eli Bar, Moshav (IL); Nimrod Meller, Tel Aviv (IL); Dror Hazan, Petah Tikva (IL)

(73) Assignee: InspireMD, Ltd., Tel Aviv (IL)

( * ) Notice: Subject to any disclaimer, the term of this patent is extended or adjusted under 35 U.S.C. 154(b) by 196 days.

(21) Appl. No.: 14/505,310

(22) Filed: Oct. 2, 2014

(65) Prior Publication Data

US 2016/0096308 A1    Apr. 7, 2016

(51) Int. Cl.
| | |
|---|---|
| *B29C 49/28* | (2006.01) |
| *B29C 49/64* | (2006.01) |
| *A61F 2/82* | (2013.01) |
| *A61F 2/958* | (2013.01) |
| *B29C 49/78* | (2006.01) |
| *G01M 3/36* | (2006.01) |
| *B29K 101/12* | (2006.01) |
| *B29L 31/00* | (2006.01) |
| *A61F 2/95* | (2013.01) |

(52) U.S. Cl.
CPC ............... *B29C 49/28* (2013.01); *A61F 2/82* (2013.01); *A61F 2/958* (2013.01); *B29C 49/64* (2013.01); *B29C 49/786* (2013.01); *G01M 3/36* (2013.01); *A61F 2002/9522* (2013.01); *A61F 2002/9583* (2013.01); *B29C 2949/78151* (2013.01); *B29C 2949/78294* (2013.01); *B29C 2949/78663* (2013.01); *B29K 2101/12* (2013.01); *B29L 2031/7546* (2013.01)

(58) Field of Classification Search
CPC .... A61F 2/82; A61F 2/958; A61F 2002/9583; A61F 2002/9522; B29C 49/64; B29C 49/786; B29C 2949/78151; B29C 2949/78294; B29C 2949/78663; B29K 2101/12; B29L 2031/7546; G01M 3/36
See application file for complete search history.

(56) References Cited

U.S. PATENT DOCUMENTS

| | | | | |
|---|---|---|---|---|
| 5,976,181 | A * | 11/1999 | Whelan | A61F 2/958 606/194 |
| 6,200,325 | B1 * | 3/2001 | Durcan | A61F 2/958 604/101.05 |
| 6,289,568 | B1 * | 9/2001 | Miller | A61M 25/0014 29/423 |

(Continued)

*Primary Examiner* — Nguyen Ha
(74) *Attorney, Agent, or Firm* — Haynes and Boone, LLP

(57) ABSTRACT

A medical stent mold includes a tube having an interior passage sized and dimensioned to receive a stent assembly disposed at least partially about a central portion of a stent balloon. The medical stent mold may also include a housing forming a chamber through which the tube extends. The tube may include a thermally conductive material and may have a body portion that extends within the chamber and an end portion that is proximate the body portion and that extends away from the housing. An inner diameter of the end portion of the tube is greater than an inner diameter of the body portion of the tube. Forced convection may be used to quickly heat and cool the tube. Methods of increasing retention of an expandable stent assembly on a stent balloon and of detecting a leak in a stent balloon are also included.

21 Claims, 6 Drawing Sheets

(56) References Cited

U.S. PATENT DOCUMENTS

| | | | |
|---|---|---|---|
| 6,561,788 B1* | 5/2003 | Gaudoin | B29C 49/48 249/102 |
| 7,763,198 B2* | 7/2010 | Knott | A61F 2/958 264/249 |
| 8,595,913 B2 | 12/2013 | Knott et al. | |
| 2003/0208254 A1* | 11/2003 | Shortt | A61F 2/958 623/1.11 |
| 2006/0229712 A1* | 10/2006 | Wilson | A61F 2/958 623/1.42 |
| 2008/0154352 A1* | 6/2008 | Goshgarian | A61F 2/958 623/1.11 |
| 2010/0241214 A1 | 9/2010 | Holzer et al. | |
| 2011/0054591 A1* | 3/2011 | Sahatjian | A61F 2/88 623/1.15 |
| 2012/0079706 A1* | 4/2012 | Knott | A61F 2/958 29/516 |
| 2013/0304183 A1* | 11/2013 | Sawada | A61F 2/91 623/1.11 |
| 2013/0331927 A1* | 12/2013 | Zheng | A61F 2/82 623/1.19 |
| 2016/0081824 A1* | 3/2016 | Harrington | B23K 26/38 29/517 |

* cited by examiner

STENT THERMOFORMING APPARATUS AND METHODS

FIELD OF THE DISCLOSURE

The present disclosure relates in general to the manufacture of a stent and more specifically, to system and methods for manufacturing a medical stent within a mold having a seamless inner surface.

BACKGROUND

The manufacture of stents, particularly in the medical field, often includes placing the medical stent within a mold. The mold and stent are then heated and an internal pressure is applied to the medical stent to force the exterior surface of the medical stent against the interior surface of the mold. The stent is then cooled so that the stent retains its expanded shape and the stent is removed from the mold. Generally, the stent is placed within a multi-segment mold, which requires a locking mechanism to ensure that the segments are stationary when the internal pressure is applied. The locking mechanism, however, may cause an unwanted tolerance range of an outer diameter of the medical stent. Additionally, the large mass of the multi-segment mold and the locking mechanism typically results in a long heating and/or cooling period of the mold, which may delay the manufacture of a subsequent medical stent and consequently increase cost and complexity of manufacture. Often, and due to the long cooling period of the mold, the internal pressure applied to the stent will be reduced, the locking mechanism will be released relatively quickly, and the multi-segment mold will be opened to allow the medical stent to cool. This may result in the medical stent deforming into an undesired shape. Conventional medical stents are sometimes tested for leaks in a subsequent method using another device after the stent is formed.

The present disclosure is directed to a medical stent thermoforming apparatus and methods that overcome one or more of the shortcomings in the prior art.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are methods and a stent assembly mold. In one or more exemplary embodiments, the mold may include a tube having an interior passage sized and dimensioned to receive a stent assembly disposed at least partially about a central portion of a stent balloon, and a housing forming a chamber through which the tube extends. In one embodiment, the tube may include a thermally conductive material. In yet another embodiment, the tube may have a body portion that extends within the chamber and an end portion that is proximate the body portion and that extends away from the housing. In an exemplary embodiment, an inner diameter of the end portion of the tube is greater than an inner diameter of the body portion of the tube. In one or more preferred embodiments, the tube may have a wall thickness of 10 micrometers to about 2000 micrometers and is at least substantially non-deformable under a pressure of up to 300 psi. In yet another preferred embodiment, the tube may have a seamless surface forming the interior passage. In another embodiment, the end portion may form a frustoconical shape. In one embodiment, the tube may include an inert material. In yet another embodiment, the end portion may be sized and shaped to receive and guide the stent assembly and stent balloon into the tube. In yet another embodiment, the interior passage may have a diameter of about 1.15 mm to about 1.35 mm.

In a further aspect, the disclosure encompasses a stent-assembly apparatus that includes a stent-assembly mold including a first tube including a heat-conductive material and having a seamless inner surface forming a passage, a heating unit disposed in proximity and fluidically connected to an outer surface of the mold, and a temperature sensor disposed in proximity to and outside the mold. In a preferred embodiment, the apparatus may also include a housing forming a chamber through which the mold and a second tube extend, in a preferred embodiment, the second tube is substantially similar to the mold and the temperature sensor is disposed within a passage formed within the second tube. In one embodiment, the heating unit forces a fluid into the chamber to heat the mold and the second tube. In yet another embodiment, the apparatus also includes a cooling unit disposed in proximity and fluidically connected to an outer surface of the mold. In one embodiment, the cooling unit forces a fluid into the chamber to cool the mold and the second tube. In a preferred embodiment, the passages formed within the mold and the second tube are fluidically isolated from the chamber. In yet another preferred embodiment, the apparatus also includes a conduit having an end fluidically coupled to a stent balloon, the end being positionable between a first location within the passage of the mold and a second location outside of the passage of the mold; and a valve positioned in proximity to the conduit to control the flow of a fluid through the conduit. In some embodiments, the mold is sized to receive a stent assembly that at least partially surrounds a portion of the stent balloon, and the end of the conduit. In yet other embodiments, the mold has a body portion that extends within the chamber and an end portion that is proximate the body portion and that extends away from the housing, wherein an inner diameter of the end portion of the stent mold is greater than an inner diameter of the body portion of the mold. In one embodiment, the first tube has a wall thickness of about 10 micrometers to about 2000 micrometers and is at least substantially non-deformable under a pressure of up to 300 psi. In yet another embodiment, the first tube is comprised at least predominantly of metal.

In yet another aspect, the disclosure encompasses a method of increasing retention of an expandable stoat assembly on a stent balloon that includes disposing an expandable stoat assembly about a central portion of a stent balloon in a pre-sized expansion zone, heating the stent balloon to at least a first temperature, and inflating the stent balloon to a first pressure to cause it to expand and correspond to the pre-sized expansion zone. In some embodiments, the method also includes cooling the stent balloon to a second temperature while maintaining the stent balloon at the first pressure in situ in the expansion zone. In yet other embodiments, inflating the stent balloon to the first pressure includes forcing a fluid through an end of a conduit that is fluidically coupled to the stent balloon. In yet another embodiment, heating the stent balloon to the first temperature includes forcing a fluid over an exterior surface of the expansion zone. In other embodiments, the method also includes measuring the temperature in a temperature monitoring zone that is substantially similar to and outside the pro-sized expansion zone and that is placed in proximity thereto and relative to a heat source to determine the first temperature and the second temperature in the pre-sized expansion zone. In one embodiment, inflating the stent balloon to the first pressure includes forcing the stent balloon and the stent assembly that at least partially surrounds the central portion of the stent balloon against the pre-sized expansion zone. In other embodiments, the stent assembly has a first end and an opposing second end, and inflating the stent balloon to the first pressure further includes contacting an exterior surface of the stent balloon with the first end and the opposing second end of the stent assembly. In another embodiment, the pre-sized expansion zone defines a cylinder.

In another aspect, the disclosure encompasses a method of detecting a leak in a stent balloon which includes disposing a stent balloon in a pre-sized expansion zone; inflating the stein balloon in the pre-sized expansion zone to a pressure that expands the balloon; isolating the pressure in the stent balloon in situ in the expansion zone, and determining whether the pressure within the stent balloon recedes below a predetermined threshold pressure over a time period. In one embodiment, the method also includes heating the stent balloon to a first temperature before inflating the stent balloon, and cooling the stent balloon to a second temperature after being inflated, while maintaining the pressure within the stent balloon. In another embodiment, a stent jacket and stent at least partially surround a central portion of the stent balloon, and inflating the stent balloon includes forcing the stent jacket against the pre-sized expansion zone. In yet another embodiment, the cooling includes forced convection.

Various of these embodiments and those further discussed herein should be understood to be applicable to various aspects of the disclosure even if described only in connection with one particular aspect.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
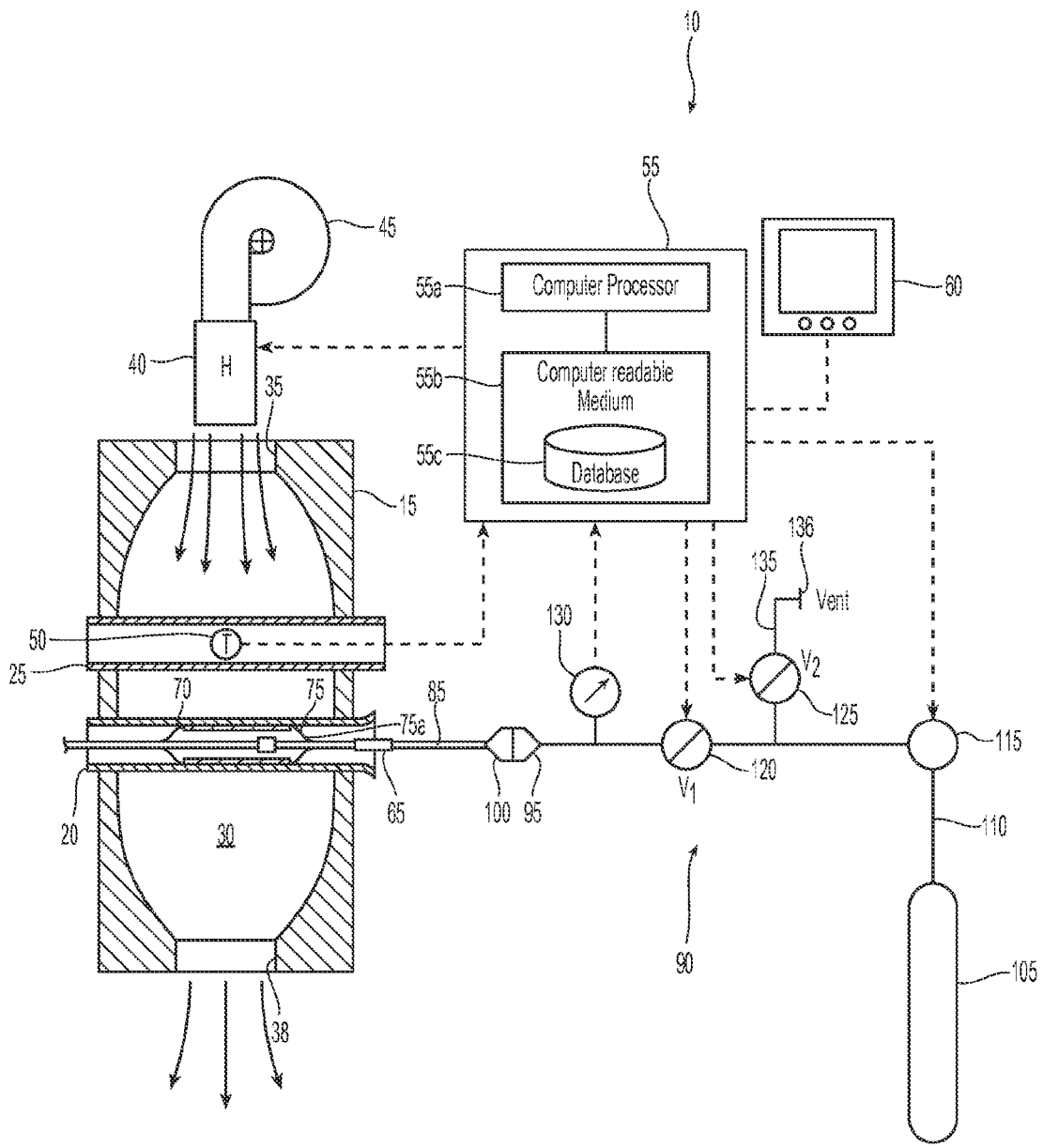
FIG. 1 is a diagrammatic view of an apparatus according to one or more aspects of the present disclosure, including a user device and a tube accommodating a stent assembly and a stent balloon.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Referring to FIG. 1, an apparatus 10 may generally include a housing 15 through which tubes 20 and 25 extend. In an exemplary embodiment, the housing 15 forms a chamber 30 having an entry opening 35 and an exit opening 38. The apparatus 10 may also include a heat exchanger 40 and blower 45 that are positioned near the entry opening 35 to force a fluid, such as a heated or cooled gas, to enter the chamber 30. In an exemplary embodiment, the tube 25 is sized to accommodate a temperature sensor 50. The temperature sensor 50 may communicate with and/or be controlled by a controller 55. In an exemplary embodiment, the controller 55 may also communicate with and/or control the heat exchanger 40 and the blower 45. The apparatus 10 may also include a user device 60 that is operably coupled to, or communicates with, the controller 55. In an exemplary embodiment, tube 20 is sized to accommodate a dolly 65 that is slideable or otherwise movable from a location at least partially within the tube 20 to a location outside of the tube 20. The dolly 65 can be used if desired to facilitate loading and unloading tube 20, or other mechanisms can be used, although the dolly 65 or mechanisms are not required. Generally and in an exemplary embodiment, the dolly 65 is slideable towards and away from the tube 20. In one or more exemplary embodiments, the stent assembly 70 at least partially surrounds a balloon 75. In one or more exemplary embodiments, a catheter 85 fluidically connects the stent balloon 75 with a pressure system 90. In one or more exemplary embodiments, the pressure system 90 may create, maintain, change, and vent a balloon pressure, or the internal radial pressure applied to the stent balloon 75. In one or more exemplary embodiment, the pressure system 90 may include a connector 95 that fluidically connects to the catheter 85 via a connector 100 located on a distal end of the catheter 85. In one or more exemplary embodiment, the connectors 95 and or 100 may be tightly sealed quick connectors or be corresponding "Luer" lock fittings, although any available connector may be used. In one or more exemplary embodiments, the pressure system 90 also includes a gas source 105 and a fluid line 110 that fluidically connects the gas source 105 to the stent balloon 75. In an exemplary embodiment, the gas source 105 may be pressurized pure nitrogen or other pressurized gas (which may include a gas mixture), but preferably the gas is inert or chemically non-reactive to the stent assembly 70, stent balloon 75, catheter 85, and tube 20. In an exemplary embodiment, the pressure system 90 may also include a regulator 115 positioned along the fluid line 110 such that the regulator 115 regulates the gas flowing through the fluid line 110, the balloon pressure, or both. The pressure system 90 may also include valves 120 and 125 and a pressure sensor 130 located along the fluid line 110 such that the valve 120 controls the flow of gas through the fluid line 110 and the valve 125 controls the flow of the gas through a vent line 135 that fluidically connects the fluid line 110 to a vent 136. In an exemplary embodiment, each of the valves 120 and 125 and the pressure sensor 130 are in communication with the controller 55, and when included can also be controlled by the controller 55. In an exemplary embodiment, the valve 120 and the pressure sensor 130 are placed along the fluid line 110 such that the gas source 105 and the regulator 115 may be isolated from the stent balloon 75 by the valve 120, while allowing the pressure sensor 130 to measure the balloon pressure.

Figure 2:
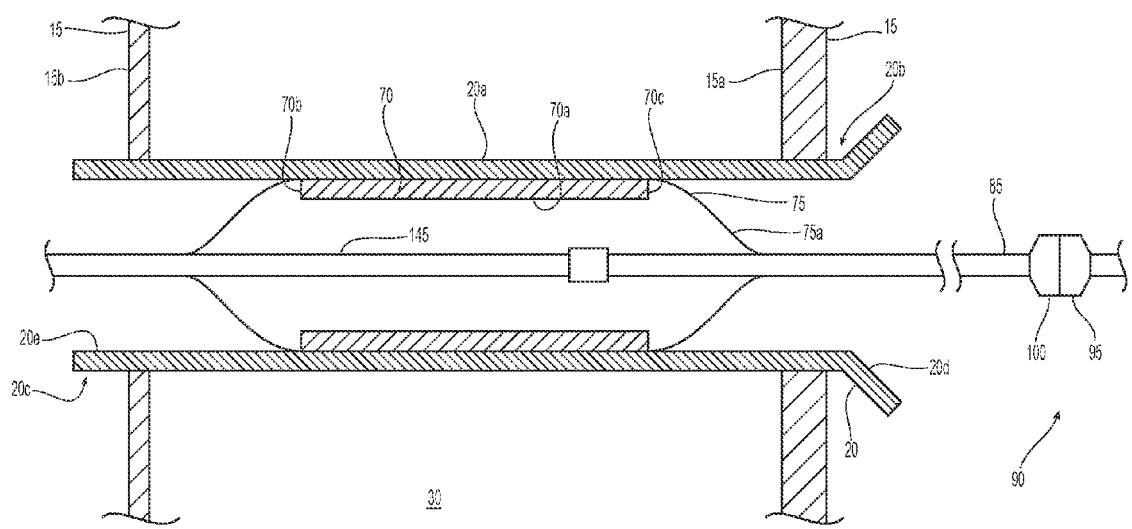
FIG. 2 is a cross sectional view of the tube accommodating the stent assembly and the stent balloon of FIG. I, according to one or more aspects of the present disclosure.

In an exemplary embodiment and as illustrated in FIG. 2, the tube 20 functions as a stent mold that forms an interior passage and has a body portion 20a that extends within the chamber 30 and an end portion 20b that is proximate the body portion 20a and that extends away from a side 15a of the exemplary housing 15. In an exemplary embodiment, the tube 20 has another end portion 20c that extends away from a side 15b of the housing 15. In one or more exemplary embodiments, the end portion 20b forms a frusto-conical shape or trumpet shape, or another shape, to facilitate guiding the stein assembly 70 and other components into the tube 20 more readily. In an exemplary embodiment, the body portion 20a extends within the chamber 30 such than the exterior surface of the body portion 20a is exposed to the gas forced into the chamber 30 by the blower 45, which blower gas is kept fluidically separate from the gas from gas source 105 as that is typically a sterile or medical grade quality gas that contacts the stent assembly 70 and other surgical components. It should be understood the blower gas may simply be untreated ambient air, or may be filtered or otherwise processed gas. In an exemplary embodiment, the tube 20 is positioned in the chamber 30 such that the blower gas forced over the exterior of the tubes 20 and 25 creates a uniform temperature along the exterior surface of the tubes 20 and 25. This can be achieved such as by placing tubes 20 and 25 in a vertical arrangement above and below each other and at the same or substantially the same distance from an outlet port of the blower 45 and exchanger 40. The end portion 20b of tube 20 forms an opening 20d that receives the stent assembly 70 and the stent balloon 75. In an exemplary embodiment, the end portion 20b has an inner diameter that is greater than an inner diameter of the body portion 20a. In an exemplary embodiment, a distal end of the stent catheter 85 may also be inserted into the opening 20d formed by the end portion 20b. In an exemplary embodiment as depicted, the end portion 20c extends away from the side 15b of the housing and forms an opening 20e. For various reasons, in some embodiments side 15b of the housing 15 can be closed, opening 20e need not be present, and the tube(s) need not extend therethrough. In such embodiments, the end portion 20c of the tube 20 (and the other tube 25) can be attached to a recess on an inner wall of side 15b sized to fit the end portion 20c, rested on a shelf, or even fixed to the inner wall of the housing 15 (not shown). In an exemplary embodiment, the interior passage of the tube 20 is fluidically isolated from the chamber 30. In an exemplary embodiment, the interior passage of the tube 20 is sized and dimensioned to receive the stent assembly 70 and the stent balloon 75. In an exemplary embodiment, the tube 20 has a seamless surface forming the interior passage. In an exemplary embodiment the tube 20 includes a thermally conductive material, such as for example, a metal (including one or more metals, such as in an alloy, composite, or combination), such as stainless steel. In an exemplary embodiment, the tube 20 is a metal, such as an inert or chemically non-reactive metal relative to the stent assembly 70, stent balloon 75, and catheter 85. In one or more exemplary embodiments, the interior passage has a diameter larger than an outer diameter of the stent 70 and the stem balloon 75. In an exemplary embodiment, the tube 20 may be a single piece of cold-drawn tube, such as for example, a hypotube, which are commercially available and used, for example, in association with conventional syringes. In an exemplary embodiment, the tube 20 is non-compliant or near non-compliant when an internal pressure is applied to the stent balloon 75. That is, the tube 20 is at least substantially non-deformable (i.e., less than 1%, less than 0.5%, less than 0.1%, or less than 0.01% in various embodiments, change of inner diameter, or is entirely non-deformable under a pressure of up to 300 psi. In one or more exemplary embodiments, the interior passage of the tube 20 may have an inner diameter between the range of 1.15-1.35 mm. In one or more exemplary embodiments, the inner diameter of the tube 20 has a tolerance of +/−10 micrometers, although typically the tolerance is less than +/−5 micrometers, and in an exemplary embodiment is less than +/−1 micrometer or even 0.1 micrometers. In an exemplary embodiment, the tube 20 is a thin-walled metallic tube that can be heated and cooled quickly using conduction, forced convection (such as directly from the blower 45 and exchanger 40), or radiation, or any combination thereof. To that end, the interior of the housing 15 facing the tubes 20 and 25 may be made of reflective material to increase radiative heating if desired, and an alternative embodiment could include heating elements arranged about the tubes 20 and 25 in place of the blower 45 and exchanger 40, permitting chamber 30 of housing 15 to be entirely sealed. In an exemplary embodiment, the tube 20 is a pre-sized expansion zone that defines a cylinder. In an exemplary embodiment, the tube 20 has a wall thickness of about 10 micrometers to about 2000 micrometers. In another embodiment, the tube 20 wall thickness is about 100 micrometers to about 1000 micrometers. In yet a further embodiment, the tube 20 wall thickness is about 200 micrometers to about 300 micrometers, for example, 210, 215, 220, 225, 230, 235, 240, 245, 250, 255, 260, 265, 270, 275, 280, 285, or 290 micrometers thick.

In an exemplary embodiment, the tube 25 is substantially identical or identical to the tube 20 therefore the tube 25 will not be described in further detail. Reference numerals used to refer to the features of the tube 25 that are substantially identical to the features of the tube 20 will correspond to the reference numerals used to refer to the features of the tube 20 except that the prefix for the reference numerals used to refer to the features of the tube 20, that is, 20, will be replaced by the prefix of the tube 25, that is,25.In an exemplary embodiment, the end portion 25b of the tube 25 does not form a frusto-conical or trumpet shape. In an exemplary embodiment, the tube 25 has an interior passage sized and dimensioned to receive the temperature sensor 50. The tube 25 extends through the chamber 30 at a location adjacent and symmetrical (in relation to air flow) to the tube 20, so that the temperature in the tube 25 is equal to, or at least corresponds to, the temperature in the tube 20. In an exemplary embodiment, the tube 25 is positioned in the chamber 30 proximate the tube 20. In an exemplary embodiment, the end portion 25b extends away from the side 15a of the housing 15 and the end portion 35a extends away from the side 15b of the housing. In an exemplary embodiment, the interior passage of the tube 25 is fluidically isolated from the chamber 30. In an exemplary embodiment, the body portion 25a extends within the chamber 30 such than the exterior surface of the body portion 25a is exposed to the gas forced into the chamber 30 by the blower 45. In an exemplary embodiment, the tube 25 is positioned in the chamber 30 such that the gas forced over the exterior of the tubes 20 and 25 creates a uniform temperature along the exterior surface of the tubes 20 and 25. In another exemplary embodiment, tube 25 may be sealed at the end(s) to simulate the arrangement of tube 20 once it is loaded with the stent assembly 70 and stent balloon 75.

In an exemplary embodiment, the temperature sensor 50 may include one or more thermocouples, a miniature thermocouple, or any other temperature sensing device. In an exemplary embodiment, the temperature sensor is accommodated in the body portion 25a of the tube 25. In an exemplary embodiment, the temperature measured by the temperature sensor 50 is equal to, or at least corresponds to, the temperature in the tube 20. In an exemplary embodiment, the temperature sensor 50 is capable of continuously monitoring the temperature within the tube 25. In one embodiment, the temperature sensor 50 is embedded or fixed within the tube 25 to minimize temperature measurement variation between different stent assemblies.

In an exemplary embodiment, the heat exchanger 40 is positioned relative to the blower 45 such that the blower 45 forces the fluid, such as air, across the heat exchanger 40 to heat or cool the gas entering the chamber 30. In an exemplary embodiment, the heat exchanger 40 may include heating coils or any other type of heating device. In an exemplary embodiment, the heat exchanger 40 and the blower 45 may be a conventional industrial hot air blower being controlled in dosed loop fashion with input from the temperature sensor 50. In an exemplary embodiment, the heat exchanger 40 is disposed in proximity and fluidically connected to an outer surface of the tube 20. In an exemplary embodiment, the heat exchanger 40 may include a refrigerant. In one embodiment, the output end of the exchanger 40 and blower 45 is connected to the housing 15 in a sealed manner, which can better control the temperature inside the housing 15. In yet another embodiment, the exchanger 40 and blower 45 are integrally formed with or embedded inside the housing 15. It should be understood that the blower 45 and exchanger 40 need not be used if another suitable heat source is provided, such as the radiative heat embodiment discussed above.

In an exemplary embodiment, the stent balloon 75 may be comprised of any elastomeric material(s), but typically is made of any surgical-grade material(s) used to form a balloon for insertion into a lumen of a patient. In an exemplary embodiment, the stent balloon 75 is an expandable balloon when an internal radial pressure is applied to the stent balloon 75. In an exemplary embodiment, the stent balloon 75 may be an angioplasty balloon.

In an exemplary embodiment, the stent assembly 70 may include any conventional medical stent. In some embodiments, the stent assembly 70 is comprised of a material which plastically deforms when a sufficient amount of radial pressure is applied to it, for example by an angioplasty balloon. In an exemplary embodiment, the stent assembly 70 is disposed about a central portion of the stent balloon 75, with the stent balloon 75 being in an at least partially unexpanded state. In one exemplary embodiment, the stent assembly 70 is "crimped" on the stent balloon 75 in a previous process and the process described herein is used to help further ensure the stent assembly 70 and stent balloon 75 do not separate. In one or more exemplar embodiments, the inflation lumen 145 extends along the length of the stent assembly 70 and is used to inflate and depressurize the stent balloon 75. In another embodiment (not shown), the inflation lumen 145 is not used and the stent balloon 75 is attached to or adjacent an end of the catheter 85, or directly to a pressure source, for inflation and depressurization. In an exemplary embodiment, the stent assembly 70 is comprised of a material that is stretchable, expandable, or both. Therefore, and in some embodiments, the stent assembly 70 is composed of a material which is either a stretchable or b) can be used to manufacture a porous support structure which is stretchable (e.g., a knitted structure). In some exemplary embodiments, the stem assembly 70 is composed of a material that is biodegradable (i.e., are broken down by the body), bioresorbable (i.e., are absorbed into the body), or any combination thereof. In an exemplary embodiment, the stent assembly 70 may be composed of a natural based material, such as for example, modified cellulose and/or collagen. In some embodiments, the stent assembly 70 may be composed of metal wires used to construct a porous support structure, including one or more of stainless steel, CoCr, or CoNi alloy, among other possibilities. In an exemplary embodiment, the metal wires are coated with at least one polymer or pharmaceutical agent, or both, as is known in the art. In some embodiments, the porous support structure is manufactured from a shape memory alloy, such as nitinol. In an exemplary embodiment, carbon fiber is added to the stent assembly 70 in order to improve strength characteristics of the stent assembly 70. In an exemplary embodiment, glass fiber is added to the stent assembly 70 in order to improve strength characteristics of the stent assembly 70. In an exemplary embodiment, a durable, resorbable and/or degradable fiber is added to the stent assembly 70 in order to improve strength and durability characteristics of the fiber during manufacture, which is degraded or resorbed or washed away to leave a thinner stent assembly 70. In an exemplary embodiment, the stent assembly structure (including the stent jacket discussed below) can include any stent or stent jacket (also referred to as a porous structure) available to those of ordinary skill in the art, including without limitation those described in U.S. Patent Publication Nos. 2009/0138070 and 2010/0241214, the entire contents of each of which is incorporated herein by express reference thereto.

In an exemplary embodiment, the stent assembly 70 includes a stent jacket (not shown) that may at least partially surround a central portion of the stent forming the support structure of stem assembly 70. In an exemplary embodiment, the stent jacket may include one or more polymer fibers. In an embodiment, the polymer chosen for use in constructing the stem jacket and/or the stent assembly 70 is elastic, biocompatible, hemocompatible, can be made not to stick to an expandable angioplasty-type balloon catheter, to stick to endothelium tissue, is selectably bio-stable and/or biodegradable, exhibits the requisite mechanical strength, is sterilizable, has a high temperature transformation zone (solid and non sticky at 37° C.), are capable of hosting an effective amount of one or more pharmaceutical agents, or can release embedded pharmaceuticals at a controlled rate, or any combination thereof. In some exemplary embodiments, other materials which exhibit some or all of these properties are optionally used to construct the stent assembly 70, typically the stent jacket portion of the stent assembly 70. In an exemplary embodiment, one or more coatings are put on the stent jacket and/or the stent in the stent assembly 70, and the coatings are comprised of materials which exhibit some or all of these properties.

In an exemplary embodiment, the polymer fiber(s) are optionally made out of any of the following materials: thermoplastic polymers including a polyolefin, for example, polyethylene terephthalate (PET), polyethylene co-vinyl acetate, polyethylene elastomer, PEO-PBT, PEO-PLA, PBMA, or any combination thereof, or polyesters, polyfluoropolymers such as PTFE, any oxidized acrylic, Carbosil® (PTG product), polyurethane such as a medical grade polycarbonate urethane, a polyamide (e.g., Nylon®), PEEK-Optima, a carboxylic acid moiety comprising one or more of a poly acrylic acid, a poly methacrylic acid, a maleic acid, a helonic acid, a taconic acid and/or combinations and/or esters of these monomers, as well as thermosetic polymers, or any combination of the foregoing. In an exemplary embodiment, the fibers are constructed of an elastomer. In an exemplary embodiment, the fibers are constructed of a coated fiber with a drug and polymer coating mixed to get a predetermined drug release characteristic, either coating over a metal and/or over a polymer fiber. In an exemplary embodiment, the fibers are constructed of other materials than the exemplary materials listed above. Exemplary polymers which are optionally used for this purpose are manufactured by Cordis®, Surmodix®, Boston Scientific®, Abbott® and Hemoteq® Polymers. In an exemplary embodiment, these polymers are selected for at least one of the reasons specified in the paragraph above. In an exemplary embodiment, the coating is used to facilitate the elution of pharmaceuticals from the stent jacket, stent, a coating over either or both, or from the entire stent assembly 70. Any suitable pharmaceutical ingredient can be eluted directly into the lumen in which the stent is deposited.

In some embodiments, any portion of the stent assembly 70 is made out of a resorbable/degradable polymer such as poly lactic-co-polyglycolic ("PLGA") copolymers, or any other degradable copolymeric combination, such as polycaprolactone ("PCL"), polygluconate, polylactic acid-polyethylene oxide copolymers, poly(hydroxybutyrate), polyanhydride, poly-phosphoester, poly(amino acids), poly-L-lactide, poly-D-lactide, polyglycolide, poly(alpha-hydroxy acid) and combinations thereof. In one exemplary embodiment, the stent of the stent assembly 70 is formed from a metal support and the stent jacket is disposed over the stent and includes one or more PET fibers arranged to provide apertures through a knit stent jacket in a size of 10 micrometers to 200 micrometers.

In an exemplary embodiment, the dolly 65 is sized to accommodate a portion of the catheter 85 and allow an operator to insert the distal end of the catheter 85 into the tube 20 to a pre-determined depth, so that the entire stent assembly 70 and balloon 75 are within the body portion 20a of the tube 20.

Figure 3:
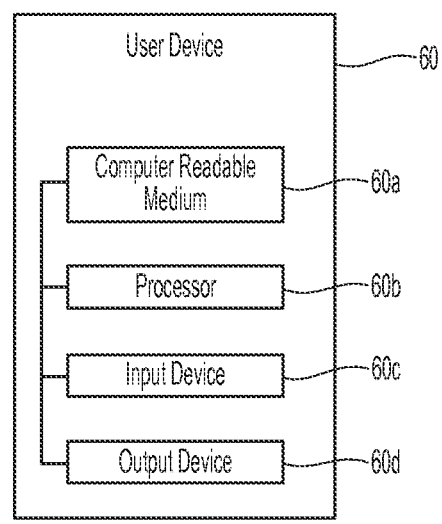
FIG. 3 is a diagrammatic illustration of the user device of FIG. 1 according to an exemplary embodiment.

In an exemplary embodiment, as illustrated in FIG. 3 with continuing reference to FIG. 1, the user device 60 includes a computer readable medium 60a, a processor 60b, an input device 60c, and an output device 60d. In an exemplary embodiment, instructions accessible to, and executable by, the processor 60b are stored in the computer readable medium 60a. In an exemplary embodiment, web browser software is stored in the computer readable medium 60a. In an exemplary embodiment, the input device 60c and the output device 60d include a graphical display, which, in several exemplary embodiments, is in the form of or includes, one or more digital displays, one or more liquid crystal displays, one or more cathode ray tube monitors, or any combination thereof. In an exemplary embodiment, the output device 60d includes a graphical display, a printer, a plotter, or any combination thereof. In an exemplary embodiment, the input device 60c is also the output device 60d, and the output device 60d is also the input device 60c, e.g., a touch-sensitive tablet computer display. In several exemplary embodiments, the user device 60 is, or includes, a personal computer, any other type of computing devices, and/or any combination thereof. In several exemplary embodiments, the user device 60 includes a plurality of user devices. In several exemplary embodiments, the user device 60 is, or at least includes the controller 55.

In an exemplary embodiment and referring back to FIG. 1, the controller 55 may include a computer processor 55a and a computer readable medium 55b operably coupled thereto. Instructions accessible to, and executable by, the computer processor 55a are stored on the computer readable medium 55b. A database 55c is also stored in the computer readable medium 55b. The controller 55 may be operably coupled to and control the function of any one or more of the heat exchanger 40, the blower 45, any additional or alternative heat source, the temperature sensor(s) 50, the user device 60, the doily 65 if included, the optional valves 120 and 125, the pressure sensor 130, and the gas regulator 115.

Figure 4:
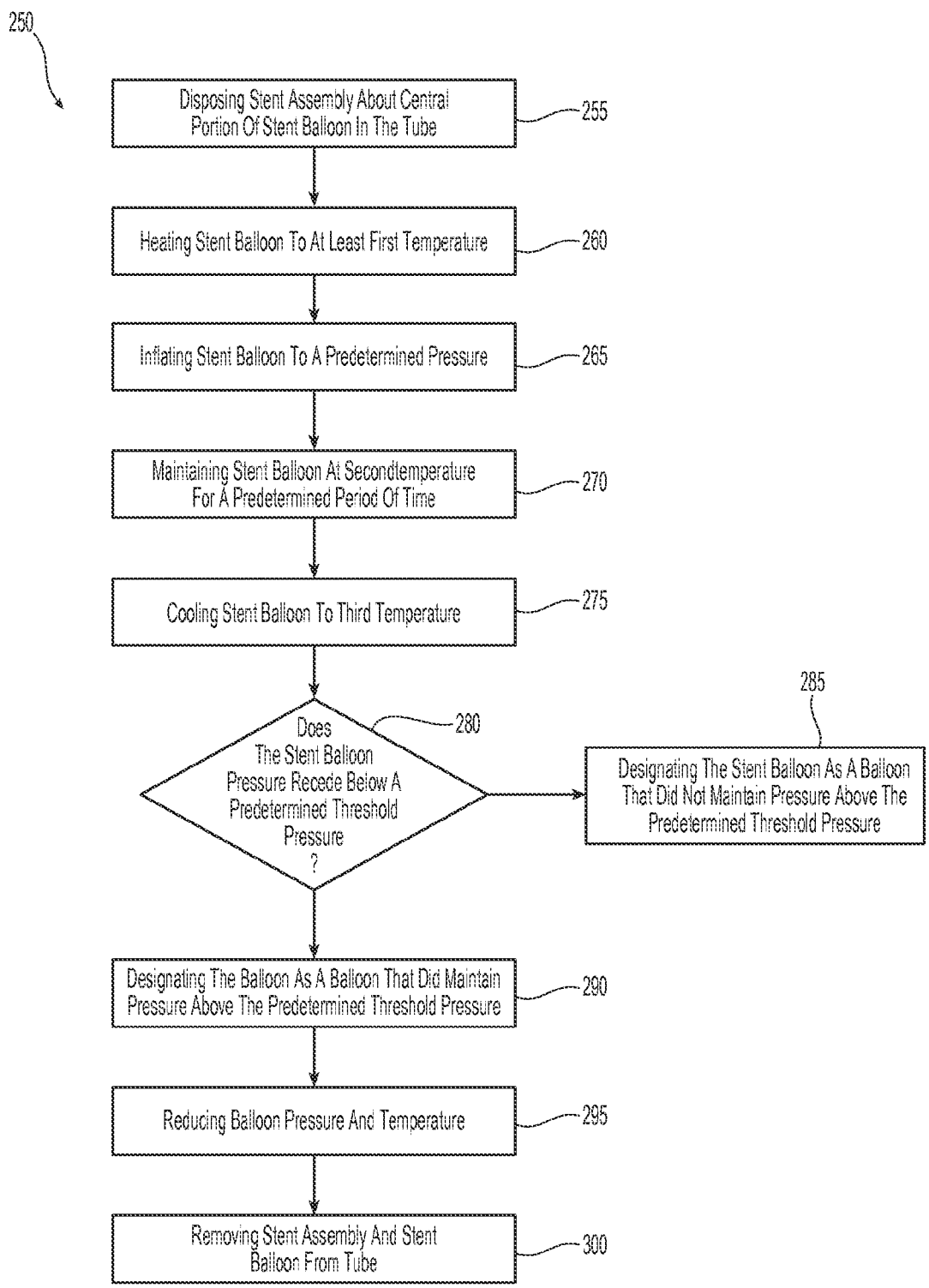
FIG. 4 is a flow chart illustration that describes a method of operating the apparatus of FIG. 1, according to an exemplary embodiment.

In an exemplary embodiment, as illustrated in FIG. 4 with continuing reference to FIGS. 1-3, a method of operating the apparatus 10 is generally referred to by the reference numeral 250. In an exemplary embodiment, the method 250 includes disposing the stent assembly 70 about a central portion of the stent balloon 75 (either inside or outside the housing) and disposing the associated stent assembly 70 and stent balloon 75 in the tube 20 at step 255; heating the stent balloon 75 to at least a first temperature at step 260; inflating the stent balloon 75 to a predetermined pressure at step 265; maintaining the stent balloon 75 at a second temperature for a predetermined period of time at step 270; cooling the stent balloon 75 to a third temperature at step 275; determining whether the balloon pressure recedes below a predetermined threshold pressure at step 280: optionally either designating the stent balloon 75 as a balloon that did not maintain pressure above the predetermined threshold pressure at step 285 or designating the stent balloon 75 as a balloon that did maintain pressure above the predetermined threshold pressure at step 290; reducing balloon pressure and temperature at step 295; and removing the stent assembly 70 and the balloon from the tube 20 at step 300. It should be understood that in one embodiment the temperature can be reduced partly or entirely back to ambient temperature while the pressure is maintained before designating the stent balloon 75 as having a leak or not based on whether it maintains the pressure above the predetermined threshold pressure. This is possible because of the thin-walled tube 20 that permits temperature to be reduced far more rapidly than a conventional mold, such as without burning or melting the materials used in the stent assembly 70 or stent balloon 75.

At the step 255, the stent assembly 70 and the stent balloon 75 are disposed in the tube 20. In an exemplary embodiment, the stent assembly 70 is disposed about a central portion of the stent balloon 75 in the unexpanded or a minimally expanded state. In an exemplary embodiment, the connector 100 is connected to the connector 95 to connect the stent balloon 75 with the pressure system 90. In an exemplary embodiment, at least a portion of the catheter 85 is accommodated within the optional dolly 65. In an exemplary embodiment, the stent assembly 70 and the stent balloon 75 are inserted into the tube 20 through the opening 20b and at least a portion of the catheter 85 is also inserted into the tube 20. In an exemplary embodiment the movement of the stent assembly 70 and the stent balloon 75 towards and away from the tube 20 is not hindered by being connected to the pressure system 90, as at least a portion of the catheter 85 is accommodated with the dolly, which is slideable towards and away from the tube 20. In an exemplary embodiment, the stent assembly 70 and the stent balloon 75 are accommodated within the body portion 20a of the tube 20. In an exemplary embodiment, the placement of the stent assembly 70 and the stent balloon 75 within the both portion 20a of the tube 20 may be performed automatically, such as under the direction of the controller 55 once initiated by the user, and removed automatically once the temperature and pressure are each reduced to acceptable levels after the process is completed for each stent assembly 70 and stent balloon 75.

Figure 5:
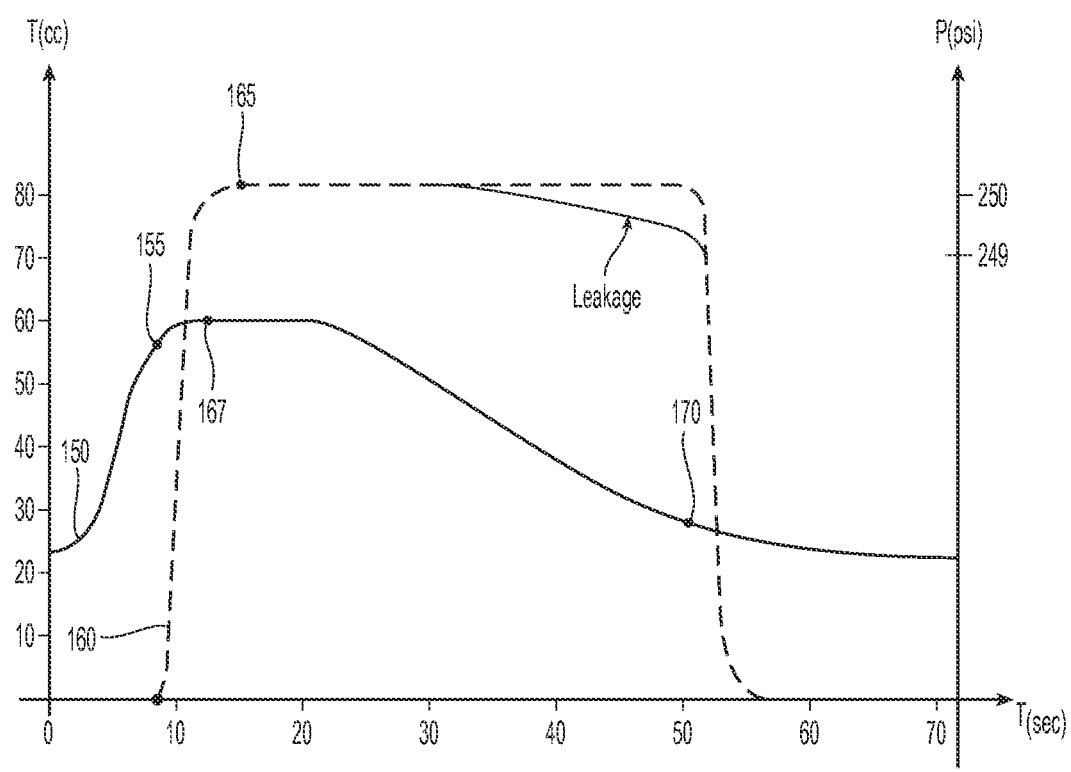
FIG. 5 is a graph showing exemplary changes to the stent assembly temperature and pressure over time during the method of FIG. 4, according to one or more aspects of the present disclosure.

At the step 260, the stent balloon 75 is heated to at least the first temperature. That is, the temperature sensor 50 measures a temperature within, the tube 20 that is at least the first temperature. In one or more embodiments, the first temperature is about 57° C. References herein to the temperature of the stent balloon 75 may be based on the temperature of the stent balloon, as based on the measurement of the temperature within the tube 25 as measured by the temperature sensor 50. In one or more exemplary embodiments, the temperature sensor 50 measures the temperature within the tube 25, which is identical or substantially identical to the temperature within the tube 20 to the stent balloon 75. In one or more exemplary embodiments, the temperature measured by the temperature sensor 50 is used to monitor the temperature of the stent balloon 75. In an exemplary embodiment, and as the tubes 20 and 25 are substantially identical, the temperatures of the tubes and the interior passages within the tubes 20 and 25 are identical or substantially identical (i.e., less than 10% difference, and in some embodiments this is a known or determined difference that can be accounted for by the controller 55). Regardless, in an exemplary embodiment the stent balloon 75 is in a softened state once the stent balloon 75 is heated to or above the first temperature. In an exemplary embodiment, heating the stent balloon 75 to the first temperature includes the blower 45 forcing air across the heat exchanger 40 and through the entry opening 35 and into the chamber 30 of the housing 15. In an exemplary embodiment, this heated air contacts the exterior surface of the tubes 20 and 25 to heat the tubes 20 and 25 and the stent balloon 75. As illustrated in FIG. 5, forcing hot air across the exterior of the tube 20 increases the temperature of the stent balloon 75, illustrated by a line 150, to the first temperature, illustrated by a point 155. However, the predetermined temperature and the predetermined temperature range is dependent upon the material of which the stent balloon 75 is comprised. In an exemplary embodiment, the first temperature is dependent upon the thermal properties of the stein balloon 75. In an exemplary embodiment, the first temperature is a temperature that permits or results in plastic deformation of the stent balloon 75.

At the step 265, the stent balloon 75 is inflated to a predetermined pressure. In an exemplary embodiment, the predetermined pressure is within a predetermined pressure range of about 240-290 psi. In an exemplary embodiment, after the temperature sensor 50 measures a temperature equal or greater than the first temperature, and while the stent balloon 75 is in the softened state due to the heating, the pressure system 90 increases the balloon pressure, illustrated by a line 160, until the balloon pressure reaches the predetermined pressure, illustrated by a point 165. In an exemplary embodiment, inflating the stent balloon 75 to the predetermined pressure includes the controller 55 opening the valve 120 and activating the regulator 115 such that the gas passes through the fluid line 110 from the gas source 105, optionally to the inflation lumen 145 or alternatively through the catheter 85, or both, to inflate the stent balloon 75. In an exemplary embodiment, the pressure sensor 130 measures the balloon pressure. In an exemplary embodiment, increasing the balloon pressure to the predetermined pressure expands the stent balloon 75 in the radial direction, or increases the diameter of the stent balloon 75, such that the stent balloon 75 is in an expanded state. That is, an exterior surface 75a of the stent balloon 75 contacts the interior diameter 70a of the stent assembly 70 and at least one of opposing end edges 70b and 70c of the stent assembly 70. In an exemplary embodiment, a "pillow" or a "shoulder" is formed in the stent balloon 75 where the exterior surface 75a of the stent balloon 75 contacts the opposing end edge 70b or 70c, or both. In an exemplary embodiment, the stent balloon 75 is in the softened state and the expanded state at the step 270. A variety of other pressure ranges are contemplated here. In an exemplary embodiment, the balloon pressure is controlled by the regulator 115, typically a self-adjusting electronic regulator. In an exemplary embodiment, the predetermined pressure is dependent upon the material of the stent balloon 75. In an exemplary embodiment, the predetermined pressure is dependent upon the thermal properties of the material forming the stent balloon 75. In an exemplary embodiment, the predetermined pressure is a pressure that results in plastic outward deformation of the stent balloon 75.

At the step 270, the stent balloon 75 is maintained at a second temperature within a predetermined temperature range for a predetermined period of time. In an exemplary embodiment, the steal balloon 75 remains in the expanded state during the step 270. In an exemplary embodiment, the second temperature, illustrated as a point 167, is 60° C. and the predetermined temperature range is 58-62° C. In an exemplary embodiment, the predetermined period of time is between 5 and 15 seconds. In another exemplary embodiment, the predetermined period of time is between 5 and 25 seconds. In another exemplary embodiment, the predetermined period of time is between 10 and 30 seconds. In an exemplary embodiment, maintaining the stent balloon 75 at a second temperature includes the controller 55 controlling the blower 45 and the heat exchanger 40 in response to the measurements obtained by the temperature sensor 50 to maintain and/or change the temperature of the stent balloon 75. In an exemplary embodiment, the balloon pressure is maintained at the predetermined pressure during the step 270. In one embodiment (not shown), the pressure is increased in the stent balloon 75 linearly as the temperature increases, typically after an initial minimum temperature threshold is reached, so that the stent balloon 75 is more pliable than at ambient temperature. In this embodiment, there are not two distinct temperatures or ranges although the maximum temperature range or second temperature is reached during the operation. In any embodiment, the pressurized stent balloon 75 typically sticks to the inner diameter of the stent assembly 75 and forms at least one pillow as discussed above.

At the step 275, the stent balloon 75 is cooled to a third temperature. In an exemplary embodiment, the third temperature is at or near room temperature, or ambient temperature. In an exemplary embodiment, the stent balloon. 75 is cooled to the third temperature in situ in the tube 20. In an exemplary embodiment, the stent balloon 75 is cooled to the third temperature in situ in the tube 20 while the balloon pressure is at the predetermined pressure. In an exemplary embodiment, the third temperature is around 24° C., as illustrated by a point 170. In an exemplary embodiment, the controller 55 controls the blower 45 and the heat exchanger 40 such that cool, or at least unheated air, is forced across the exterior surface of the body portion 20a of the tube 20 to cool the stent balloon 75 and accompanying components. In an exemplary embodiment, the stent balloon 75 becomes harder (less pliable) when cooled to the third temperature. In an exemplary embodiment the stent balloon 75 is cooled while in the expanded state such that the exterior surface 75a of the balloon remains in contact with at least one of the opposing end surfaces 70b and 70c, and typically along a length of the inner diameter of the stent assembly 75, even after the balloon pressure is reduced. Therefore, and in an exemplary embodiment, the balloon is "hardened" with the one or two shoulders or pillows so that the exterior surface 75a of the stent balloon 75 contacts at least one of the opposing end surface 70b and 70c to increase a stent retention force when the stent assembly 70 is later inserted into a patient's lumen at the distal end of a catheter, such as catheter 85. It should be understood that the stent assembly 70 and stent balloon 75 may be removed from catheter 85 for shipping, assembly with a different catheter or other insertion device, or the like, or may be retained on the same catheter 85 for immediate use, storage, or shipment for later remote use.

At the step 280, the controller 55, using the pressure sensor 130, determines whether the balloon pressure has receded below a predetermined threshold pressure. In an exemplary embodiment, the pressure system 90 isolates the stent balloon 75 from the pressure source 105 and the regulator 115 by closing the valve 120. In an exemplary embodiment, the isolation of the stent balloon 75 occurs after a predetermine period of time or upon the temperature of the stent balloon 75 receding below a predetermined threshold temperature, such as for example 50° C. In an exemplary embodiment, the predetermined threshold temperature may be greater than the third temperature. In an exemplary embodiment, the pressure sensor 130 measures the balloon pressure after the stent balloon 75 is isolated, and the controller 55 determines whether the balloon pressure drops below the predetermined, pressure threshold. In an exemplary embodiment, the stein balloon 75 is isolated for 5 seconds, 10 seconds, 15, seconds, or more. In an exemplary embodiment, the predetermined pressure threshold is approximately 1 psi, 5 psi, or 10 psi lower (or even lower, such as 75%, 50%, or 2% of the imparted pressure) than the predetermined pressure. In an exemplary embodiment, the threshold pressure is 249 psi. However, a variety of threshold pressures are contemplated here. If the controller 55 determines that the balloon pressure has receded below the threshold pressure, the next step is step 285. If the controller 55 determines that the balloon pressure has not receded below the threshold pressure, the next step is step 290. In one or more exemplary embodiment, the balloon pressure receding below the threshold may indicate a damaged balloon, such as for example, a strut balloon 75 that has a leak. In an exemplary embodiment, the step 280 may occur simultaneously with or during the step 270 or the step 275. That is, the pressure system 90 may isolate the stent balloon 75 from the pressure source 105 and the regulator 115 any time after the stent balloon 75 reaches the second temperature.

At the step 285, the controller 55 designates the stent balloon 75 as a balloon that did not maintain pressure above the predetermined threshold. In one exemplary embodiment, the output device 60d of the user device 60 displays a notification that the stent balloon 75 is an "unacceptable" balloon or a FAIL. In an exemplary embodiment, an unacceptable balloon may be a balloon that has a leak. In this embodiment, the stent balloon 75 may be removed from the stent assembly 70 in case it is possible to re-use the stent assembly 70 in the process with a fresh stent balloon 75.

At the step 290, the controller 55 designates the stent balloon 75 as a balloon that did maintain pressure above the predetermined threshold. In one exemplary embodiment, the output device 60d of the user device 60 displays a notification that the stent balloon 75 is an "acceptable" balloon. Of course, a green light or color could be used, as a red light or color could be used above for the unacceptable balloon, and a variety of other suitable distinguishing characteristics can be used together or alternatively.

At the step 295 and after either the step 285 or the step 290, the balloon pressure is reduced to ambient or atmospheric pressure and the balloon further cools to room temperature. In an exemplary embodiment, the controller 55 opens the valves 120 and 125 to allow gas to pass from the stent balloon 75 and through the vent line 135 and out of the vent 136. The heat exchanger 40 and blower 45 may continue forcing cool, or at least unheated air, across the exterior surface of the tube 20 to further cool the stent balloon 75 to room temperature it the stent balloon 75 has not already reached room temperature.

At the step 300, the stent assembly 70 and the stent balloon 75 are removed from the tube 20. The stent assembly 70 and the stent balloon 75 may be removed by an operator, or automatically after the output device 60d of the user device 60 displays a notification that the stent assembly 70 and the stent balloon 75 may be removed from the tube 20.

In an exemplary embodiment, the method 250 is used to create a relatively quick temperature rise and a plateau to the second temperature for a desired length of time followed by a quick cooling by air flow at ambient temperature. In an exemplary embodiment, the method 250 results in the stent balloon 75 being inflated to the expanded state while in a softened state, and then the stein balloon 75 being hardened by cooling the stent balloon 75 to a third temperature while in the expanded state. In an exemplary embodiment, the method results in the shoulders or pillows being formed to increase the stent retention force. While FIG. 2 depicts such shoulders in a particular configuration, it should be understood that each pillow may have a different or independent shape, and may be in any shape desired. For example, in one embodiment the pillows may be rounded (not shown), such that a bump exists adjacent the end of the stent but the balloon does not contact the stent except at the stent end edges 70b, 70c near or below the outer surface of the stent. In another embodiment, the pillow, or shoulder, is radially uniform. In another embodiment, the leading edge of the stent balloon 75 contacts the inner surface of the tube 20 along a length (as opposed to a point). Various configurations can be provided, but preferably the pillow/stent combination will minimize lateral slippage between the stent and balloon 75 along an axial length of the stent.

In an exemplary embodiment, the method 250 may be completed in between 45 and 60 seconds. Of course, longer times can be used if desired. In an exemplary embodiment, the method 250 results in a quickly heated and quickly cooled stent mold. In an exemplary embodiment, the method 250 results in a forced heating and a forced cooling of the mold, or the tube 20, and the stent balloon 75 while maintaining the stent balloon 75 at the predetermined pressure. In an exemplary embodiment, the method 250 results in a balloon 75 and stent assembly 70 having an exterior diameter that falls within a tolerance range, such as for example, +/−0.01 mm or less. In an exemplary embodiment, the tube 20 is a seamless, one-piece tube 20 independent of a locking mechanism. In an exemplary embodiment, the seamless, smooth interior diameter of the tube 20 decreases the likelihood of damaging the stent assembly 70 and/or the stent balloon 75 by snagging or deforming any mesh, fibers, elastomer, coating material, or fabric that may be attached to or part or be part of the stent assembly 70. In an exemplary embodiment, the method 250 may be used to detect a leak in the stent balloon 75, particularly in one embodiment while the stent balloon 75 is still "in the mold", i.e., in the tube 20. This can advantageously avoid the need for a second device to conduct leak detection/balloon acceptability test at a later time.

In an exemplary embodiment, data relating to predetermined limits may be stored in the database 55c. In an exemplary embodiment, the predetermined limits may be the predetermined temperature range and the predetermined pressure range. In an exemplary embodiment, the controller 55 may determine whether the temperature as measured by the temperature sensor 50 exceeds the predetermined temperature range and if so, may cause the output device 60d of the user device 60 to display a notification that the stent balloon 75 was exposed to conditions outside of the predetermined limits. In an exemplary embodiment, the controller 55 may determine whether the pressure as measured by the pressure sensor exceeds the predetermined pressure range and if so, may cause the output device 60d of the user device 60 to display a notification that the stent balloon 75 was exposed to conditions outside of the predetermined limits. In an exemplary embodiment, the controller 55 may designate the stent balloon 75 as a stent balloon 75 that was exposed to conditions outside of the predetermined limits. In an exemplary embodiment and when the balloon 75 is exposed to conditions outside of the predetermined limits, the controller 55 may designate the stent balloon 75 as "unacceptable."

In an exemplary embodiment, the steps 260-300 are performed automatically after an operator inputs or selects a start command from the input display 60c of the user device 60.

Figure 6:
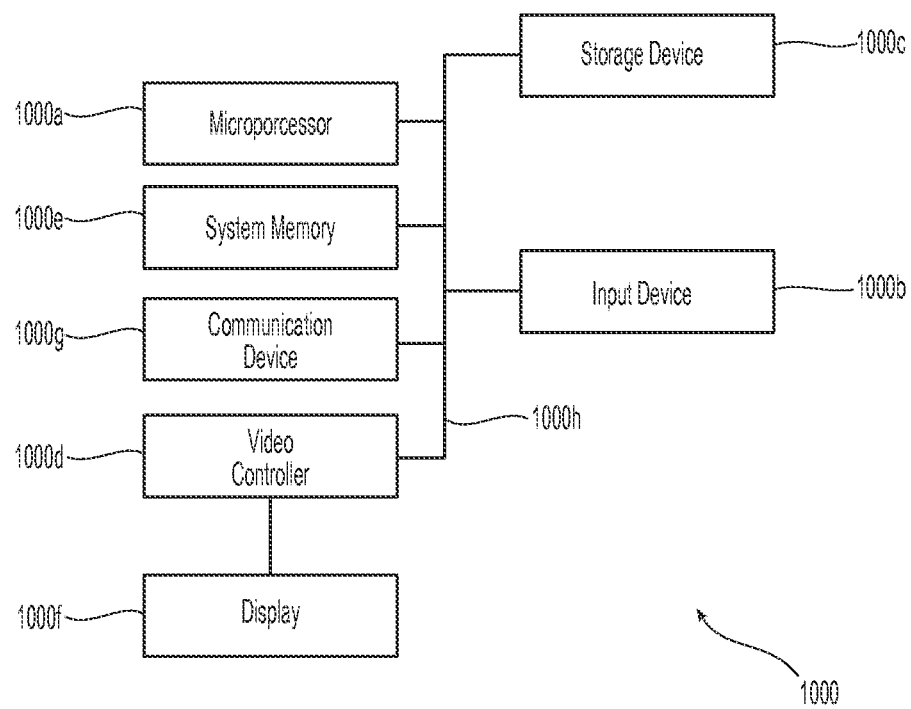
FIG. 6 is a diagrammatic illustration of a node for implementing one or more exemplary embodiments of the present disclosure, according to an exemplary embodiment.

In an exemplary embodiment, as illustrated in FIG. 6 with continuing reference to FIGS. 1-5, an illustrative node 1000 for implementing one or more embodiments of one or more of the above-described networks, elements, methods, steps, or any combination thereof, is depicted. The node 1000 includes a microprocessor 1000a, an input device 1000b, a storage device 1000c, a video controller 1000d, a system memory 1000e, a display 1000f, and a communication device 1000g all interconnected by one or more buses 1000h. In several exemplary embodiments, the storage device 1000c may include a floppy drive, hard drive, CD-ROM, optical drive, any other form of storage device and/or any combination thereof. In several exemplary embodiments, the storage device 1000c may include, and/or be capable of receiving, a floppy disk, CD-ROM, DVD-ROM, or any other form of computer-readable medium that may contain executable instructions. In several exemplary embodiments, the communication device 1000g may include a modem, network card, or any other device to enable the node to communicate with other nodes. In several exemplary embodiments, any node represents a plurality of interconnected (whether by intranet or Internet) computer systems, including without limitation, personal computers, mainframes, PDAs, and cell phones.

In several exemplary embodiments, one or more of the heat exchanger 40, the blower 45, the temperature sensor 50, the pressure sensor 130, the valve 120, the valve 125, the pressure regulator 115, the user device 60, the controller 55 includes the node 1000, or components thereof, or one or more nodes that are substantially similar to the node 1000 or components thereof.

In several exemplary embodiments, a computer system typically includes at least hardware capable of executing machine readable instructions, as well as the software for executing acts (typically machine-readable instructions) that produce a desired result. In several exemplary embodiments, the computer system may include hybrids of hardware and software, as well as computer sub-systems.

In several exemplary embodiments, hardware generally includes at least processor-capable platforms, such as client-machines (also known as personal computers or servers), and hand-held processing devices (such as smart phones, personal digital assistants (PDAs), or personal computing devices (PCDs), for example). In several exemplary embodiments, hardware may include any physical device that is capable of storing machine-readable instructions, such as memory or other data storage devices. In several exemplary embodiments, other forms of hardware include hardware sub-systems, including transfer devices such as modems, modem cards, ports, and port cards, for example.

In several exemplary embodiments, software includes any machine code stored in any memory medium, such as RAM or ROM, and machine code stored on other devices (such as floppy disks, flash memory, or a CD ROM, for example). In several exemplary embodiments, software may include source or object code. In several exemplary embodiments, software encompasses any set of instructions capable of being executed on a node such as, for example, on a client machine or server.

In several exemplary embodiments, combinations of software and hardware could also be used for providing enhanced functionality and performance for certain embodiments of the present disclosure. In an exemplary embodiment, software functions may be directly manufactured into a silicon chip. Accordingly, it should be understood that combinations of hardware and software are also included within the definition of the computer system and are thus envisioned by the present disclosure as possible equivalent structures and equivalent methods.

In several exemplary embodiments, computer readable mediums include, for example, passive data storage, such as a random access memory (RAM) as well as semi-permanent data storage such as a compact disk read only memory (CD-ROM). One or more exemplary embodiments of the present disclosure may be embodied in the RAM of a computer to transform a standard computer into a new specific computing machine. In several exemplary embodiments, data structures are defined organizations of data that may enable an embodiment of the present disclosure. In an exemplary embodiment, a data structure may provide an organization of data, or an organization of executable code. In several exemplary embodiments, data signals could be carried across transmission mediums and store and transport various data structures, and, thus, may be used to transport an embodiment of the present disclosure.

In several exemplary embodiments, a database may be any standard or proprietary database software, such as Oracle, Microsoft Access, SyBase, or DBase II, for example. In several exemplary embodiments, the database may have fields, records, data, and other database elements that may be associated through database specific software. In several exemplary embodiments, data may be mapped. In several exemplary embodiments, mapping is the process of associating one data entry with another data entry. In an exemplary embodiment, the data contained in the location of a character file can be mapped to a field in a second table. In several exemplary embodiments, the physical location of the database is not limiting, and the database may be distributed. In an exemplary embodiment, the database may exist remotely from the server, and run on a separate platform. In an exemplary embodiment, the database may be accessible across the Internet. In several exemplary embodiments, more than one database may be implemented.

In an exemplary embodiment, the computer readable medium 55b includes a plurality of instructions stored thereon, the instructions being executable by at least the computer processor 55a to execute and control the above-described operation of the apparatus 10. In an exemplary embodiment, the computer readable medium 55b includes a plurality of instructions stored thereon, the instructions being executable by at least the computer processor 55a to execute the method 250.

In several exemplary embodiments, the elements and teachings of the various illustrative exemplary embodiments may be combined in whole or in part in some or all of the illustrative exemplary embodiments. In addition, one or more of the elements and teachings of the various illustrative exemplary embodiments may be omitted, at least in part, and/or combined, at least in part, with one or more of the other elements and teachings of the various illustrative embodiments, Any spatial references such as for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not necessarily limit the specific orientation or location of the structure described above.

In several exemplary embodiments, while different steps, processes, and procedures are described as appearing as distinct acts, one or more of the steps, one or more of the processes, and/or one or more of the procedures may also be performed in different orders, simultaneously and/or sequentially. In several exemplary embodiments, the steps, processes and/or procedures may be merged into one or more steps, processes and/or procedures.

In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

In another aspect, the disclosure encompasses a thermoformed, unpressurized, stent-balloon assembly that includes a longitudinally extending stent having a first end and an opposing second end, the longitudinally extending stent forming an interior passage between the first end and the second end, a releasable thermoformed stent balloon at least partially disposed in the interior passage and affixed to the stent, wherein a first portion of the stent balloon is in contact with the first end of the stent and a second portion of the stent balloon is in contact with the second end of the stein so as to prevent premature separation of the stent under ambient temperature and pressure. For clarity, ambient temperature and pressure simply mean the respective temperature and pressure of the environment in which the stent-balloon assembly is presently located, e.g., in a normal room at sea level, 1 atm and 68° F. or 20° C. without external application of heat or refrigeration. In one embodiment, the stent and the stent balloon are inhibited from lateral movement relative to each other, in another embodiment, the first and second portions of the stent balloon contact the entire first and second ends of the stent. The stent balloon is affixed to the stent typically without adhesive or external structure to cause retention—the thermoforming of the balloon material into the apertures of the stent itself and around the ends of the stent itself typically cause the affixation. Thus, the stent-balloon assembly is typically adhesive-free.

The apparatus described herein permits such a thermoformed, unpressurized, stent-balloon assembly to be provided, and to retain the association between the stent and the stent balloon even after the combination is heated to permit them to releasably join together and preferably even after the pressure is removed as described herein. Thus, while the stent and balloon assembly of the thermoformed stent-balloon assembly may shift, they are retained together because they are temporarily affixed to each other while the stent is in a retracted (i.e., not fully deployed, or radially expanded) state. They can be released when desired, such as by a surgeon after implantation in a lumen of a patient. This can be achieved, for example, by inflating the stent balloon to expand the stent as fully as desired in a radial direction, and then deflating the balloon. Once the stent is fully deployed in a radially expanded state, the balloon more readily comes loose or can be detached such as by one or more cords and then removed along with a catheter or any other components temporarily inserted m a patient for the purpose of fully delivering the stent to a desired location.

Although several exemplary embodiments have been described in detail above, the embodiments described are exemplary only and are not limiting, and those skilled in the art will readily appreciate that many other modifications, changes and/or substitutions are possible in the exemplary embodiments without materially departing from the novel teachings and advantages of the present disclosure. Accordingly, all such modifications, changes and/or substitutions are intended to be included within the scope of this disclosure as defined in the following claims.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to allow the reader to quickly ascertain the nature of the technical disclosure. It is submitted with the understanding that it will not be used to interpret or limit the scope or meaning of the claims.

What is claimed is:
1. A stent assembly mold, comprising:
a tube having an interior passage sized and dimensioned to receive a stent assembly disposed at least partially about a central portion of a stent balloon; and
a housing forming a chamber through which the tube extends;

wherein the tube comprises a thermally conductive material; and wherein the tube has a body portion that extends within the chamber and an end portion that is proximate the body portion and that extends away from the housing, wherein an inner diameter of the end portion of the tube is greater than an inner diameter of the body portion of the tube.

2. The stent assembly mold of claim 1, which further comprises a heating element configured to heat a fluid in the chamber so as to heat the tube.

3. The stent assembly mold of claim 1, wherein the tube has a wall thickness of 10 micrometers to about 2000 micrometers and is at least substantially non-deformable under a pressure of up to 300 psi.

4. The stent assembly mold of claim 1, wherein the tube has a seamless surface forming the interior passage.

5. The stent assembly mold of claim 1, wherein the end portion forms a frusto-conical shape.

6. The stent assembly mold of claim 1, wherein the tube comprises an inert material.

7. The stent assembly mold of claim 1, wherein the end portion is sized and shaped to receive and guide the stent assembly and stent balloon into the tube.

8. The stent assembly mold of claim 1, wherein the interior passage has a diameter of about 1.15 mm to about 1.35 mm.

9. A stent-assembly apparatus, which comprises:
- a stent-assembly mold comprising a first tube including a heat-conductive material and having a seamless inner surface forming a passage;
- a heating unit disposed in proximity and fluidically connected to an outer surface of the mold;
- a temperature sensor disposed in proximity to and outside the mold;
- a housing forming a chamber through which the mold and a second tube extend;
- wherein the second tube is at least substantially similar to the mold;
- wherein the temperature sensor is disposed within a passage formed within the second tube; and
- wherein the heating unit forces a fluid into the chamber to heat the mold and the second tube.

10. The stent-assembly apparatus of claim 9, which further comprises:
- a cooling unit disposed in proximity and fluidically connected to an outer surface of the mold;
- wherein the cooling unit forces a fluid into the chamber to cool the mold and the second tube.

11. The stent-assembly apparatus of claim 9, wherein the passages formed within the mold and the second tube are fluidically isolated from the chamber.

12. The stent-assembly apparatus of claim 9, further comprising:
- a conduit having an end fluidically coupled to a stent balloon, the end being positionable between a first location within the passage of the mold and a second location outside of the passage of the mold; and
- a valve positioned in proximity to the conduit to control the flow of a fluid through the conduit;
- wherein the mold is sized to receive a stent assembly that at least partially surrounds a portion of the stent balloon, and the end of the conduit.

13. The stent-assembly apparatus of claim 9, wherein the mold has a body portion that extends within the chamber and an end portion that is proximate the body portion and that extends away from the housing, wherein an inner diameter of the end portion of the mold is greater than an inner diameter of the body portion of the mold.

14. The stent-assembly apparatus of claim 9, wherein the first tube has a wall thickness of about 10 micrometers to about 2000 micrometers and is at least substantially non-deformable under a pressure of up to 300 psi.

15. The stent-assembly apparatus of claim 9, wherein the first tube is comprised at least predominantly of metal.

16. A method of increasing retention of an expandable stent assembly on a stent balloon, which comprises:
- disposing an expandable stent assembly about a central portion of a stent balloon in a pre-sized expansion zone;
- heating the stent balloon to at least a first temperature;
- inflating the stent balloon to a first pressure to cause it to expand and correspond to the pre-sized expansion zone;
- cooling the stent balloon to a second temperature while maintaining the stent balloon at the first pressure in situ in the expansion zone; and
- measuring the temperature in a temperature monitoring zone that is substantially similar to and outside the pre-sized expansion zone and that is placed in proximity thereto and relative to a heat source to determine the first temperature and the second temperature in the pre-sized expansion zone.

17. The method of claim 16, wherein inflating the stent balloon to the first pressure comprises forcing a fluid through an end of a conduit that is fluidically coupled to the stent balloon.

18. The method of claim 16, wherein heating the stent balloon to the first temperature comprises forcing a fluid over an exterior surface of the expansion zone.

19. The method of claim 16, wherein inflating the stent balloon to the first pressure comprises forcing the stent balloon and the stent assembly that at least partially surrounds the central portion of the stent balloon against the pre-sized expansion zone.

20. The method of claim 19, wherein the stent assembly has a first end and an opposing second end, wherein inflating the stent balloon to the first pressure further comprises contacting an exterior surface of the stent balloon with the first end and the opposing second end of the stent assembly.

21. The method of claim 16, wherein the pre-sized expansion zone defines a cylinder.

* * * * *